United States Patent
Cha et al.

(10) Patent No.: US 9,782,393 B2
(45) Date of Patent: *Oct. 10, 2017

(54) PHARMACEUTICAL COMPOSITIONS AND METHODS FOR TREATING CANCER AND BIOMARKERS FOR DRUG SCREENING

(71) Applicant: NATIONAL DEFENSE MEDICAL CENTER, Taipei (TW)

(72) Inventors: Tai-Lung Cha, Taipei (TW); Sun-Yran Chang, Taipei (TW); Guang-Huan Sun, Taipei (TW); Chung-Chih Lin, Taipei (TW); Yi-Ta Tsai, Taipei (TW)

(73) Assignee: National Defense Medical Center, Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 15/174,393

(22) Filed: Jun. 6, 2016

(65) Prior Publication Data

US 2016/0339004 A1 Nov. 24, 2016

Related U.S. Application Data

(62) Division of application No. 14/617,318, filed on Feb. 9, 2015, now Pat. No. 9,393,234, which is a division of application No. 13/903,504, filed on May 28, 2013, now abandoned.

(51) Int. Cl.
*A61K 31/44* (2006.01)
*A61K 31/404* (2006.01)
*G01N 33/50* (2006.01)

(52) U.S. Cl.
CPC ............ *A61K 31/44* (2013.01); *A61K 31/404* (2013.01); *G01N 33/5005* (2013.01); *G01N 33/5011* (2013.01); *G01N 2333/912* (2013.01); *G01N 2800/52* (2013.01)

(58) Field of Classification Search
None
See application file for complete search history.

(56) References Cited

U.S. PATENT DOCUMENTS 9,393,234 B2 * 7/2016 Cha .................... A61K 31/44
2011/0243957 A1 10/2011 Echeverria Moran et al.

OTHER PUBLICATIONS

Chen et al., "Superoxide is the major reactive oxygen species regulating autophagy," Cell Death Differ., vol. 16, pp. 1040-1052 (2009).

Eisenberg-Lerner et al., "PKD is a kinase of Vps34 that mediates ROS-induced autophagy downstream of DAPk," Cell Death Differ., vol. 19, pp. 788-797 (2012).
Eisenberg-Lerner et al., "DAP kinase regulates JNK signaling by binding and activating protein kinase D under oxidative stress," Cell Death Differ., vol. 14, pp. 1908-1915 (2007).
Widau et al., "Protein Phosphatase 2A (PP2A) Holoenzymes Regulate Death-associated Protein Kinase (DAPK) in Ceramide-induced Anoikis," J. Biol. Chem., vol. 285, No. 18, pp. 13827-13838 (Apr. 30, 2010).
Shang et al., "Death-associated Protein Kinase as a Sensor of Mitochondrial Membrane Potential: Role of Lysosome in Mitochondrial Toxin-Induced Cell Death," J. Biol. Chem., vol. 280, No. 41, pp. 34644-34653 (Oct. 14, 2005).
Prahallad et al., "Unresponsiveness of colon cancer to BRAF (V600E) inhibition through feedback activation of EGFR," Nature, vol. 483, pp. 100-103 (Mar. 1, 2012).
Xing et al., "Concurrent loss of the PTEN and RB1 tumor suppressors attenuates RAF dependence in melanomas harboring $^{V600E}$BRAF," Oncogene, vol. 31, pp. 446-457 (2012).
Kim et al., "TNF-α-induced ROS production triggering apoptosis is directly linked to Romo1 and Bcl-$X_L$," Cell Death Differ., vol. 17, pp. 1420-1434 (2010).
Sawada et al., "Molecular mechanisms of TNF-α-induced ceramide formation in human glioma cells;P53-mediated oxidant stress-dependent and -independent pathways," Cell Death Differ., vol. 11, pp. 997-1008 (2004).
Vanlangenakker et al., "cIAP1 and TAK1 protect cells from TNF-induced necrosis by preventing RIP1/RIP3-dependent reactive oxygen species production," Cell Death Differ., vol. 18, pp. 656-665 (2011).

(Continued)

*Primary Examiner* — Anna Pagonakis
(74) *Attorney, Agent, or Firm* — Muncy, Geissler, Olds & Lowe, P.C.

(57) ABSTRACT

A pharmaceutical composition comprising sorafenib and GW5074. Said combination therapy inhibits cancer cell growth via c-Raf-PP2A-DAPK signaling transduction pathway in either in vitro or in preclinical animal model for orthotopic spontaneous kidney cancer which simulates clinical symptoms. Formation of the bond between c-Raf and GW5074 leads to conformational change which consequently increases the affinity between sorafenib and c-Raf. Binding with the specific drug target facilitates serine 308 dephosphorylation of DAPK by PP2A and induces necrosis in cancer cells. Serine 308 of DAPK protein may also be used as a biomarker for drug screening. This study provides a novel pharmaceutical composition comprising sorafenib and GW5074, a protein complex target consisting of c-Raf and DAPK for drug designing, as well as biomarkers including c-Raf protein, DAPK protein and phosphorylation status of DAPK for drug screening.

20 Claims, 18 Drawing Sheets

(56) References Cited

OTHER PUBLICATIONS

Abraham et al., "Raf-1-associated Protein Phosphatase 24 as a Positive Regulator of Kinase Activation," J. Biol. Chem., vol. 275, pp. 22300-22304 (2000).
Ciardiello et al., "EGFR Antagonists in Cancer Treatment," N. Engl. J. Med., vol. 358, pp. 1160-1174 (Mar. 13, 2008).
Carmeliet et al., "Molecular mechanisms and clinical applications of angiogenesis," Nature, vol. 473, pp. 298-307 (May 19, 2011).
Francia et al., "Mouse models of advanced spontaneous metastasis for experimental therapeutics," Nat. Rev. Cancer, vol. 11, pp. 135-141 (Feb. 2011).
Begley et al., "Raise standards for preclinical cancer research," Nature, vol. 483, pp. 531-533 (Mar. 29, 2012).
Singh et al., "Modeling and predicting clinical efficacy for drugs targeting the tumor milieu," Nat. Biotechnol., vol. 30, No. 7, pp. 648-657 (Jul. 2012).
Joseph et al., "The RAF inhibitor PLX4032 inhibits ERK signaling and tumor cell proliferation in a V600E BRAF-selective manner," Proc. Natl. Acad. Sci. USA, vol. 107, No. 33, pp. 14903-14908 (Aug. 17, 2010).
Johannessen et al.,"COT drives resistance to RAF inhibition through MAP kinase pathway reactivation," Nature, vol. 468, pp. 968-972 (Dec. 16, 2010).
Straussman et al., "Tumour micro-environment elicits innate resistance to RAF inhibitors through HGF secretion," Nature, vol. 487, pp. 500-504 (Jul. 26, 2012).
Poulikakos et al., "RAF inhibitor resistance is mediated by dimerizationof aberrantly spliced BRAF (V600E)," Nature, vol. 480, pp. 387-390 (Dec. 15, 2011).
Poulikakos et al., "RAF inhibitors transactive RAF dimers and ERK signalling in cells with wild-type BRAF," Nature, vol. 464, pp. 427-430 (Mar. 18, 2010).
Raj et al., "Selective killing of cancer cells by a small molecule targeting the stress response to ROS," Nature, vol. 475, pp. 231-234 (Jul. 14, 2011).
Guenebeaud et al., "The Dependence Receptor UNC5H2/B Triggers Apoptosis via PP2A-Mediated Dephosphorylation of DAP Kinase," Mol Cell, vol. 40, pp. 863-876 (Dec. 22, 2010).
Brummer et al., "Identification of novel ERK-mediated feedback phosphorylation sites at the C-terminus of B-Raf," Oncogene, vol. 22, pp. 8823-8834 (2003).
Ritt et al., "Impact of Feedback Phosphorylation and Raf Heterodimerization on Normal and Mutant B-Raf Signaling," Mol. Cell Biol., vol. 30, pp. 806-819 (2010).
Paraiso et al., "Recovery of phospho-ERK activity allows melanoma cells to escape from BRAF inhibitor therapy," J. Cancer, vol. 102, pp. 1724-1730 (2010).
Alavi et al., "Role of Raf in Vascular Protection from Distinct Apoptotic Stimuli," Science, vol. 301, pp. 94-96 (2003).

* cited by examiner

SEQUENCE LISTING

<160> NUMBER OF SEQ ID NOS: 6

<210> SEQ ID NO 1
<211> LENGTH: 648
<212> TYPE: PRT
<213> ORGANISM: Homo sapiens
<300> PUBLICATION INFORMATION:
<308> DATABASE ACCESSION NUMBER: GenPept/ NP_002871.1
<309> DATABASE ENTRY DATE: 2013-04-21

<400> SEQUENCE: 1

```
Met Glu His Ile Gln Gly Ala Trp Lys Thr Ile Ser Asn Gly Phe Gly
 1               5                  10                  15

Phe Lys Asp Ala Val Phe Asp Gly Ser Ser Cys Ile Ser Pro Thr Ile
             20                  25                  30

Val Gln Gln Phe Gly Tyr Gln Arg Ala Ser Asp Gly Lys Leu
         35                  40                  45

Thr Asp Pro Ser Lys Thr Ser Asn Thr Ile Arg Val Phe Leu Pro Asn
 50                  55                  60

Lys Gln Arg Thr Val Val Asn Val Arg Asn Gly Met Ser Leu His Asp
65                   70                  75                  80

Cys Leu Met Lys Ala Leu Lys Val Arg Gly Leu Gln Pro Glu Cys Cys
                 85                  90                  95

Ala Val Phe Arg Leu Leu His Glu His Lys Gly Lys Lys Ala Arg Leu
            100                 105                 110

Asp Trp Asn Thr Asp Ala Ala Ser Leu Ile Gly Glu Glu Leu Gln Val
        115                 120                 125

Asp Phe Leu Asp His Val Pro Leu Thr Thr His Asn Phe Ala Arg Lys
130                 135                 140

Thr Phe Leu Lys Leu Ala Phe Cys Asp Ile Cys Gln Lys Phe Leu Leu
145                 150                 155                 160

Asn Gly Phe Arg Cys Gln Thr Cys Gly Tyr Lys Phe His Glu His Cys
                165                 170                 175

Ser Thr Lys Val Pro Thr Met Cys Val Asp Trp Ser Asn Ile Arg Gln
            180                 185                 190

Leu Leu Leu Phe Pro Asn Ser Thr Ile Gly Asp Ser Gly Val Pro Ala
        195                 200                 205

Leu Pro Ser Leu Thr Met Arg Arg Met Arg Glu Ser Val Ser Arg Met
    210                 215                 220

Pro Val Ser Ser Gln His Arg Tyr Ser Thr Pro His Ala Phe Thr Phe
225                 230                 235                 240

Asn Thr Ser Ser Pro Ser Ser Glu Gly Ser Leu Ser Gln Arg Gln Arg
                245                 250                 255

Ser Thr Ser Thr Pro Asn Val His Met Val Ser Thr Thr Leu Pro Val
            260                 265                 270

Asp Ser Arg Met Ile Glu Asp Ala Ile Arg Ser His Ser Glu Ser Ala
        275                 280                 285

Ser Pro Ser Ala Leu Ser Ser Pro Asn Asn Leu Ser Pro Thr Gly
    290                 295                 300

Trp Ser Gln Pro Lys Thr Pro Val Pro Ala Gln Arg Glu Arg Ala Pro
305                 310                 315                 320

Val Ser Gly Thr Gln Glu Lys Asn Lys Ile Arg Pro Arg Gly Gln Arg
                325                 330                 335

Asp Ser Ser Tyr Tyr Trp Glu Ile Glu Ala Ser Glu Val Met Leu Ser
            340                 345                 350
```

```
Thr Arg Ile Gly Ser Gly Ser Phe Gly Thr Val Tyr Lys Gly Lys Trp
            355                 360                 365
His Gly Asp Val Ala Val Lys Ile Leu Lys Val Val Asp Pro Thr Pro
            370                 375                 380
Glu Gln Phe Gln Ala Phe Arg Asn Glu Val Ala Val Leu Arg Lys Thr
385                 390                 395                 400
Arg His Val Asn Ile Leu Leu Phe Met Gly Tyr Met Thr Lys Asp Asn
                405                 410                 415
Leu Ala Ile Val Thr Gln Trp Cys Glu Gly Ser Ser Leu Tyr Lys His
                420                 425                 430
Leu His Val Gln Glu Thr Lys Phe Gln Met Phe Gln Leu Ile Asp Ile
            435                 440                 445
Ala Arg Gln Thr Ala Gln Gly Met Asp Tyr Leu His Ala Lys Asn Ile
450                 455                 460
Ile His Arg Asp Met Lys Ser Asn Asn Ile Phe Leu His Glu Gly Leu
465                 470                 475                 480
Thr Val Lys Ile Gly Asp Phe Gly Leu Ala Thr Val Lys Ser Arg Trp
                485                 490                 495
Ser Gly Ser Gln Gln Val Glu Gln Pro Thr Gly Ser Val Leu Trp Met
            500                 505                 510
Ala Pro Glu Val Ile Arg Met Gln Asp Asn Asn Pro Phe Ser Phe Gln
            515                 520                 525
Ser Asp Val Tyr Ser Tyr Gly Ile Val Leu Tyr Glu Leu Met Thr Gly
            530                 535                 540
Glu Leu Pro Tyr Ser His Ile Asn Asn Arg Asp Gln Ile Ile Phe Met
545                 550                 555                 560
Val Gly Arg Gly Tyr Ala Ser Pro Asp Leu Ser Lys Leu Tyr Lys Asn
                565                 570                 575
Cys Pro Lys Ala Met Lys Arg Leu Val Ala Asp Cys Val Lys Lys Val
                580                 585                 590
Lys Glu Glu Arg Pro Leu Phe Pro Gln Ile Leu Ser Ser Ile Glu Leu
            595                 600                 605
Leu Gln His Ser Leu Pro Lys Ile Asn Arg Ser Ala Ser Glu Pro Ser
            610                 615                 620
Leu His Arg Ala Ala His Thr Glu Asp Ile Asn Ala Cys Thr Leu Thr
625                 630                 635                 640
Thr Ser Pro Arg Leu Pro Val Phe
                645

<210> SEQ ID NO 2
<211> LENGTH: 1430
<212> TYPE: PRT
<213> ORGANISM: Homo sapiens
<300> PUBLICATION INFORMATION:
<308> DATABASE ACCESSION NUMBER: GenPept/ NP_004929.2
<309> DATABASE ENTRY DATE: 2013-04-17

<400> SEQUENCE: 2

Met Thr Val Phe Arg Gln Glu Asn Val Asp Asp Tyr Tyr Asp Thr Gly
1               5                   10                  15
Glu Glu Leu Gly Ser Gly Gln Phe Ala Val Val Lys Lys Cys Arg Glu
            20                  25                  30
Lys Ser Thr Gly Leu Gln Tyr Ala Ala Lys Phe Ile Lys Lys Arg Arg
        35                  40                  45
Thr Lys Ser Ser Arg Arg Gly Val Ser Arg Glu Asp Ile Glu Arg Glu
    50                  55                  60
```

-continued

Val Ser Ile Leu Lys Glu Ile Gln His Pro Asn Val Ile Thr Leu His
 65                  70                  75                  80

Glu Val Tyr Glu Asn Lys Thr Asp Val Ile Leu Ile Leu Glu Leu Val
                 85                  90                  95

Ala Gly Gly Glu Leu Phe Asp Phe Leu Ala Glu Lys Glu Ser Leu Thr
            100                 105                 110

Glu Glu Glu Ala Thr Glu Phe Leu Lys Gln Ile Leu Asn Gly Val Tyr
        115                 120                 125

Tyr Leu His Ser Leu Gln Ile Ala His Phe Asp Leu Lys Pro Glu Asn
    130                 135                 140

Ile Met Leu Leu Asp Arg Asn Val Pro Lys Pro Arg Ile Lys Ile Ile
145                 150                 155                 160

Asp Phe Gly Leu Ala His Lys Ile Asp Phe Gly Asn Glu Phe Lys Asn
                165                 170                 175

Ile Phe Gly Thr Pro Glu Phe Val Ala Pro Glu Ile Val Asn Tyr Glu
            180                 185                 190

Pro Leu Gly Leu Glu Ala Asp Met Trp Ser Ile Gly Val Ile Thr Tyr
        195                 200                 205

Ile Leu Leu Ser Gly Ala Ser Pro Phe Leu Gly Asp Thr Lys Gln Glu
    210                 215                 220

Thr Leu Ala Asn Val Ser Ala Val Asn Tyr Glu Phe Glu Asp Glu Tyr
225                 230                 235                 240

Phe Ser Asn Thr Ser Ala Leu Ala Lys Asp Phe Ile Arg Arg Leu Leu
                245                 250                 255

Val Lys Asp Pro Lys Lys Arg Met Thr Ile Gln Asp Ser Leu Gln His
            260                 265                 270

Pro Trp Ile Lys Pro Lys Asp Thr Gln Gln Ala Leu Ser Arg Lys Ala
        275                 280                 285

Ser Ala Val Asn Met Glu Lys Phe Lys Lys Phe Ala Ala Arg Lys Lys
    290                 295                 300

Trp Lys Gln Ser Val Arg Leu Ile Ser Leu Cys Gln Arg Leu Ser Arg
305                 310                 315                 320

Ser Phe Leu Ser Arg Ser Asn Met Ser Val Ala Arg Ser Asp Asp Thr
                325                 330                 335

Leu Asp Glu Glu Asp Ser Phe Val Met Lys Ala Ile Ile His Ala Ile
            340                 345                 350

Asn Asp Asp Asn Val Pro Gly Leu Gln His Leu Leu Gly Ser Leu Ser
        355                 360                 365

Asn Tyr Asp Val Asn Gln Pro Asn Lys His Gly Thr Pro Pro Leu Leu
    370                 375                 380

Ile Ala Ala Gly Cys Gly Asn Ile Gln Ile Leu Gln Leu Leu Ile Lys
385                 390                 395                 400

Arg Gly Ser Arg Ile Asp Val Gln Asp Lys Gly Gly Ser Asn Ala Val
                405                 410                 415

Tyr Trp Ala Ala Arg His Gly His Val Asp Thr Leu Lys Phe Leu Ser
            420                 425                 430

Glu Asn Lys Cys Pro Leu Asp Val Lys Asp Lys Ser Gly Glu Met Ala
        435                 440                 445

Leu His Val Ala Ala Arg Tyr Gly His Ala Asp Val Ala Gln Leu Leu
    450                 455                 460

Cys Ser Phe Gly Ser Asn Pro Asn Ile Gln Asp Lys Glu Glu Glu Thr
465                 470                 475                 480

```
Pro Leu His Cys Ala Ala Trp His Gly Tyr Tyr Ser Val Ala Lys Ala
                485                 490                 495
Leu Cys Glu Ala Gly Cys Asn Val Asn Ile Lys Asn Arg Glu Gly Glu
            500                 505                 510
Thr Pro Leu Leu Thr Ala Ser Ala Arg Gly Tyr His Asp Ile Val Glu
            515                 520                 525
Cys Leu Ala Glu His Gly Ala Asp Leu Asn Ala Cys Asp Lys Asp Gly
            530                 535                 540
His Ile Ala Leu His Leu Ala Val Arg Arg Cys Gln Met Glu Val Ile
545                 550                 555                 560
Lys Thr Leu Leu Ser Gln Gly Cys Phe Val Asp Tyr Gln Asp Arg His
                565                 570                 575
Gly Asn Thr Pro Leu His Val Ala Cys Lys Asp Gly Asn Met Pro Ile
            580                 585                 590
Val Val Ala Leu Cys Glu Ala Asn Cys Asn Leu Asp Ile Ser Asn Lys
            595                 600                 605
Tyr Gly Arg Thr Pro Leu His Leu Ala Ala Asn Asn Gly Ile Leu Asp
            610                 615                 620
Val Val Arg Tyr Leu Cys Leu Met Gly Ala Ser Val Glu Ala Leu Thr
625                 630                 635                 640
Thr Asp Gly Lys Thr Ala Glu Asp Leu Ala Arg Ser Glu Gln His Glu
                645                 650                 655
His Val Ala Gly Leu Leu Ala Arg Leu Arg Lys Asp Thr His Arg Gly
            660                 665                 670
Leu Phe Ile Gln Gln Leu Arg Pro Thr Gln Asn Leu Gln Pro Arg Ile
            675                 680                 685
Lys Leu Lys Leu Phe Gly His Ser Gly Ser Gly Lys Thr Thr Leu Val
            690                 695                 700
Glu Ser Leu Lys Cys Gly Leu Leu Arg Ser Phe Phe Arg Arg Arg Arg
705                 710                 715                 720
Pro Arg Leu Ser Ser Thr Asn Ser Ser Arg Phe Pro Pro Ser Pro Leu
                725                 730                 735
Ala Ser Lys Pro Thr Val Ser Val Ser Ile Asn Asn Leu Tyr Pro Gly
            740                 745                 750
Cys Glu Asn Val Ser Val Arg Ser Arg Ser Met Met Phe Glu Pro Gly
            755                 760                 765
Leu Thr Lys Gly Met Leu Glu Val Phe Val Ala Pro Thr His His Pro
            770                 775                 780
His Cys Ser Ala Asp Asp Gln Ser Thr Lys Ala Ile Asp Ile Gln Asn
785                 790                 795                 800
Ala Tyr Leu Asn Gly Val Gly Asp Phe Ser Val Trp Glu Phe Ser Gly
                805                 810                 815
Asn Pro Val Tyr Phe Cys Cys Tyr Asp Tyr Phe Ala Ala Asn Asp Pro
            820                 825                 830
Thr Ser Ile His Val Val Phe Ser Leu Glu Glu Pro Tyr Glu Ile
            835                 840                 845
Gln Leu Asn Gln Val Ile Phe Trp Leu Ser Phe Leu Lys Ser Leu Val
            850                 855                 860
Pro Val Glu Glu Pro Ile Ala Phe Gly Gly Lys Leu Lys Asn Pro Leu
865                 870                 875                 880
Gln Val Val Leu Val Ala Thr His Ala Asp Ile Met Asn Val Pro Arg
                885                 890                 895
Pro Ala Gly Gly Glu Phe Gly Tyr Asp Lys Asp Thr Ser Leu Leu Lys
```

-continued

```
                900             905             910
Glu Ile Arg Asn Arg Phe Gly Asn Asp Leu His Ile Ser Asn Lys Leu
            915             920             925

Phe Val Leu Asp Ala Gly Ala Ser Gly Ser Lys Asp Met Lys Val Leu
        930             935             940

Arg Asn His Leu Gln Glu Ile Arg Ser Gln Ile Val Ser Val Cys Pro
945             950             955             960

Pro Met Thr His Leu Cys Glu Lys Ile Ile Ser Thr Leu Pro Ser Trp
            965             970             975

Arg Lys Leu Asn Gly Pro Asn Gln Leu Met Ser Leu Gln Gln Phe Val
        980             985             990

Tyr Asp Val Gln Asp Gln Leu Asn Pro Leu Ala Ser Glu Glu Asp Leu
        995             1000            1005

Arg Arg Ile Ala Gln Gln Leu His Ser Thr Gly Glu Ile Asn Ile
    1010            1015            1020

Met Gln Ser Glu Thr Val Gln Asp Val Leu Leu Leu Asp Pro Arg
    1025            1030            1035

Trp Leu Cys Thr Asn Val Leu Gly Lys Leu Leu Ser Val Glu Thr
    1040            1045            1050

Pro Arg Ala Leu His His Tyr Arg Gly Arg Tyr Thr Val Glu Asp
    1055            1060            1065

Ile Gln Arg Leu Val Pro Asp Ser Asp Val Glu Glu Leu Leu Gln
    1070            1075            1080

Ile Leu Asp Ala Met Asp Ile Cys Ala Arg Asp Leu Ser Ser Gly
    1085            1090            1095

Thr Met Val Asp Val Pro Ala Leu Ile Lys Thr Asp Asn Leu His
    1100            1105            1110

Arg Ser Trp Ala Asp Glu Glu Asp Glu Val Met Val Tyr Gly Gly
    1115            1120            1125

Val Arg Ile Val Pro Val Glu His Leu Thr Pro Phe Pro Cys Gly
    1130            1135            1140

Ile Phe His Lys Val Gln Val Asn Leu Cys Arg Trp Ile His Gln
    1145            1150            1155

Gln Ser Thr Glu Gly Asp Ala Asp Ile Arg Leu Trp Val Asn Gly
    1160            1165            1170

Cys Lys Leu Ala Asn Arg Gly Ala Glu Leu Leu Val Leu Leu Val
    1175            1180            1185

Asn His Gly Gln Gly Ile Glu Val Gln Val Arg Gly Leu Glu Thr
    1190            1195            1200

Glu Lys Ile Lys Cys Cys Leu Leu Leu Asp Ser Val Cys Ser Thr
    1205            1210            1215

Ile Glu Asn Val Met Ala Thr Thr Leu Pro Gly Leu Leu Thr Val
    1220            1225            1230

Lys His Tyr Leu Ser Pro Gln Leu Arg Glu His Glu Pro
    1235            1240            1245

Val Met Ile Tyr Gln Pro Arg Asp Phe Phe Arg Ala Gln Thr Leu
    1250            1255            1260

Lys Glu Thr Ser Leu Thr Asn Thr Met Gly Gly Tyr Lys Glu Ser
    1265            1270            1275

Phe Ser Ser Ile Met Cys Phe Gly Cys His Asp Val Tyr Ser Gln
    1280            1285            1290

Ala Ser Leu Gly Met Asp Ile His Ala Ser Asp Leu Asn Leu Leu
    1295            1300            1305
```

-continued

```
Thr Arg Arg Lys Leu Ser Arg Leu Leu Asp Pro Pro Asp Pro Leu
    1310                1315                1320

Gly Lys Asp Trp Cys Leu Leu Ala Met Asn Leu Gly Leu Pro Asp
    1325                1330                1335

Leu Val Ala Lys Tyr Asn Thr Ser Asn Gly Ala Pro Lys Asp Phe
    1340                1345                1350

Leu Pro Ser Pro Leu His Ala Leu Leu Arg Glu Trp Thr Thr Tyr
    1355                1360                1365

Pro Glu Ser Thr Val Gly Thr Leu Met Ser Lys Leu Arg Glu Leu
    1370                1375                1380

Gly Arg Arg Asp Ala Ala Asp Phe Leu Leu Lys Ala Ser Ser Val
    1385                1390                1395

Phe Lys Ile Asn Leu Asp Gly Asn Gly Gln Glu Ala Tyr Ala Ser
    1400                1405                1410

Ser Cys Asn Ser Gly Thr Ser Tyr Asn Ser Ile Ser Ser Val Val
    1415                1420                1425

Ser Arg
    1430

<210> SEQ ID NO 3
<211> LENGTH: 21
<212> TYPE: RNA
<213> ORGANISM: Artificial Sequence
<220> FEATURE:
<223> OTHER INFORMATION: synthetic

<400> SEQUENCE: 3
caagaaacgu uagcaaaugu u                                        21

<210> SEQ ID NO 4
<211> LENGTH: 21
<212> TYPE: RNA
<213> ORGANISM: Artificial Sequence
<220> FEATURE:
<223> OTHER INFORMATION: synthetic

<400> SEQUENCE: 4
cauuugcuaa cguuucuugu u                                        21

<210> SEQ ID NO 5
<211> LENGTH: 21
<212> TYPE: RNA
<213> ORGANISM: Artificial Sequence
<220> FEATURE:
<223> OTHER INFORMATION: synthetic

<400> SEQUENCE: 5
ggucaaggau ccaaagaagu u                                        21

<210> SEQ ID NO 6
<211> LENGTH: 21
<212> TYPE: RNA
<213> ORGANISM: Artificial Sequence
<220> FEATURE:
<223> OTHER INFORMATION: synthetic

<400> SEQUENCE: 6
cuucuuugga uccuugaccu u                                        21
```

PHARMACEUTICAL COMPOSITIONS AND METHODS FOR TREATING CANCER AND BIOMARKERS FOR DRUG SCREENING

CROSS-REFERENCE TO RELATED APPLICATIONS

This application is a divisional of co-pending application Ser. No. 14/617,318, filed Feb. 9, 2015, which is a Divisional of application Ser. No. 13/903,504, filed on May 28, 2013, now abandoned, for which priority is claimed under 35 U.S.C. §120, the entire contents of all of which are hereby incorporated by reference.

BACKGROUND OF THE INVENTION

1. Field of the Invention

The present invention relates to a pharmaceutical composition for treating cancer, comprising sorafenib and GW5074. The invention also discloses a method for dissociating a protein complex consisting of c-Raf and DAPK by drugs, which can then be used as targets for designing new drugs. Additionally, the invention further provides a method for screening drugs utilizing proteins c-Raf and DAPK as well as the phosphorylation status of DAPK.

2. Description of the Prior Art

Activation of the proto-oncogenes or deficiency of the tumor suppressor genes often leads to cancer cell development. Ras is a proto-oncogene and activation of Ras protein is normally triggered by receptor tyrosine kinase (TKIs) on the cell membrane. Activated Ras protein binds with RAF and subsequently transmits the signal downstream to activate the MAPK pathway which, in turn, regulates cell growth as well as cell differentiation. Activated Grb-sos protein arising from binding of a growth factor to its receptor on the cell membrane leads to phosphorylation of downstream Ras-GDP protein, and the resulting Ras-GTP then binds to the N-terminus of Raf protein and activates Raf, which further regulates the activation of ERK through phosphorylation of MEK. Next, activated ERK enters the cell nucleus and induces cancer cell proliferation. Therefore, countless drugs that are designed specifically against these proto-oncogenes such as these tyrosine kinase inhibitors (TKIs) were generated, only to discover that many cancer patients developed drug resistance during the treatment. Consequently, combination therapy that specifically targets the signaling transduction pathway of tyrosine kinase has become a common treatment method.

Angiogenesis as well as cell proliferation play essential roles in tumor growth. Binding of vascular endothelial growth factor (VEGF-A) released from cancer cells in vast amounts to vascular endothelial growth factor receptor (VEGFR-2) on the surface of the endothelial cells of a tumor activates the signaling transduction pathway of Raf/mitogen-activated protein kinase (MEK)/extracellular signal-regulated kinase (ERK) which in turn induces angiogenesis of endothelial cells. Meanwhile, the Ras-ERK pathway also facilitates cancer cell proliferation. In addition, loss of regulation of the Ras-Raf-ERK pathway has been shown in a number of tumor cell lines. Thus, VEGF and Raf may be the best targets for inhibition of tumor growth.

Sorafenib (Nexavar®, BAY 43-9006, Bayer HealthCare Pharmaceuticals) is an oral Multi-Kinase Inhibitor commonly used for treating various cancers. Sorafenib can inhibit proteins such as Raf, VEGF receptor, platelet-derived growth factor (PDGF) receptor, KIT and Fms-like tyrosine kinase-3 (FLT-3). A number of studies have indicated that sorafenib inhibits tumor growth by inhibiting Raf signaling pathway in different cancer cells while suppressing proliferation of the endothelia cells surrounding cancer cells through inhibition of VEGF as well as PDGF signaling pathways, and subsequently induces cancer cell death. The design and test results of these drugs are ideal. However, after few years of clinical applications, it was unfortunate discovered that, although the tumor size at the early stage of treatment was efficiently inhibited by sorafenib, the drug not only cannot eradicate the tumor completely, but causes serious side effects. Moreover, these treated cancer cells developed drug resistance after prolonged treatment. Additionally, in recent years, certain studies have shown that inhibition of Raf signaling pathway in cancer cells leads to reduced inhibition of sorafenib due to alternative regulation by different molecules in cancer cells. Most importantly, some evidence further indicated that the inhibition effects of sorafenib on cancer cells may not be regulated by the Raf pathway. Hence, the aforementioned imperfections need to be further improved.

SUMMARY OF THE INVENTION

Treating cancer patients with sorafenib at an early stage can indeed efficiently inhibit tumor size. Nonetheless, this treatment cannot eliminate tumors completely. Even worse, severe side effects usually appear after prolonged treatment and tumor cells may consequently develop drug resistance. This indicates that the current treatment is not an effective method and further improvements are urgently required. Therefore, the present invention reveals certain discoveries, comprising: (1) a novel combination therapy of sorafenib and GW5074; (2) a target for new drug design to effectively kill cells by triggering cell necroptosis induced by dissociation of c-Raf and DAPK; and (3) a biomarker used for drug screening utilizing proteins c-Raf and DAPK as well as the phosphorylation status of DAPK.

In one aspect, the present invention provides a pharmaceutical composition for treating cancer, comprising sorafenib and GW5074 (3-(3,5-Dibromo-4-hydroxy-benzylidene)-5-iodo-1,3-dihydro-indol-2-one).

According to the invention, the composition is administered separately, concurrently, or orderly.

According to the invention, the cancer comprises renal cell carcinoma, prostate cancer, breast cancer, lung cancer, cervical carcinoma, oral cancer, glioma, urothelial cell carcinoma, or melanoma.

According to the invention, the pharmaceutical composition further includes pharmaceutically acceptable salts or vehicles. The aforementioned vehicles comprise excipients, diluents, thickeners, fillers, binders, disintegrants, lubricants, oil or non-oil agents, surfactants, suspending agents, gelling agents, adjuvants, preservatives, antioxidants, stabilizers, coloring agents or spices thereof.

According to the invention, the pharmaceutical composition is for oral administration, immersion, injection, topical application or patch administration.

According to the pharmaceutical composition of the invention, GW5074 binds to c-Raf protein (SEQ ID NO: 1) and induces conformational change of c-Raf, which consequently increases the binding affinity of sorafenib to altered c-Raf protein and disassembles c-Raf from DAPK protein complex.

In another aspect, the present invention reveals the applications of any one of the abovementioned pharmaceutical compositions for treating cancer.

In another aspect, the present invention also provides methods for preparation of drugs that separate a protein complex using compounds, wherein at least one of the compounds can be used for dissociation of a protein complex and said protein complex consists of c-Raf (SEQ ID NO: 1) and DAPK (SEQ ID NO: 2).

According to the invention, the composition comprises sorafenib and GW5074.

In one aspect, the invention discloses a method for drug screening utilizing a biomarker and comprises a provided specimen and at least one of the following: the expression status and/or phosphorylation status of a biomarker prior to administration of the drugs. Drugs that are positively correlated with growth inhibition of cells after administration are deemed suitable drugs. The biomarker is selected from at least one of the following: protein c-Raf (SEQ ID NO: 1) and protein DAPK (SEQ ID NO: 2).

According to the invention, the phosphorylation site of c-Raf protein and DAPK protein is serine 338 (Ser338) and serine 308 (Ser308), respectively.

According to the invention, the specimen comprises ascites, blood, urine, feces, sputum, mucosal cells, gastric fluid, bile, or detached cancer tissues collected after a surgery.

According to the invention, the drugs are sorafenib and GW5074.

In one embodiment, the present invention also discloses the use of a biomarker for drug screening, wherein the biomarker is at least one of the following: protein c-Raf (SEQ ID NO: 1) and protein DAPK (SEQ ID NO: 2).

According to the invention, the phosphorylation site of c-Raf protein and DAPK protein is serine 338 (Ser338) and serine 308 (Ser308), respectively.

According to the invention, the drugs are sorafenib and GW5074.

According to the invention, the use further includes detection of at least one of the following: the expression status and phosphorylation status of the biomarker prior to administration of drugs, and those drugs that are positively correlated with growth inhibition observed after treatment are deemed suitable drugs.

The concept of the novel combination therapy is combining sorafenib, which is originally an antiangiogenic drug, with GW5074, which is a c-Raf inhibitor. When administered singularly at a low-dose (sorafenib at 5 uM or GW5074 at 10 uM), none of the two drugs showed growth inhibition. However, the combination of these two originally non-toxic drugs produced cytotoxicity, considerably reduced side effects resulting from an effective dose of sorafenib, as well as inhibited cancer cell growth. The novel combination therapy revealed in the present invention uncovers a unique molecular mechanism demonstrating that these two drugs destroy the protein complex of c-Raf and DAPK by binding to c-Raf, which in turn leads to cell apoptosis and can be used as new targets for future drug design. Studies indicated that the combination therapy was most effective in cancer cells with highly phosphorylated c-Raf s338, while exhibiting poor inhibition effects on human cancer cells with low DAPK protein expression or lower phosphorylated DAPK-s308.

The drug or drug for screening that dissociates c-Raf and DAPK proteins is a drug combination comprising sorafenib and GW5074.

The term "pharmaceutically acceptable excipient" is used herein to refer to any physiologically inert or pharmacologically inactive substance known to a person skilled in the art that is physically or chemically compatible with either sorafenib or GW5074. Pharmaceutically acceptable excipients include, but are not limited to, polymers, resins, plasticizers, fillers, lubricants, diluents, binders, disintegrants, solvents, cosolvents, surfactants, preservatives, sweeteners, flavoring agents, pharmaceutically grade dyes or pigments, and viscosity agents.

In this application, the term "pharmaceutical composition" is a solid or liquid composition whose form, concentration and degree of purity are suitable for administration to a patient (such as a human or an animal patient) and may induce desired physiological changes after its administration. A pharmaceutical composition is typically sterile and/or non-pyrogenic.

As used herein, the term "combination" describes materials that combining combine two or more compounds and/or drugs (also called ingredients in this application). The term "combined" and "combining" have the same meaning.

Binding of two or more compounds/drugs in a composition can be physical or non-physical. The examples of a compound/drug composition that was bound physically include compositions (e.g. a single mixture) that contains two or more mixed compounds/drugs (e.g. in the same single dosage), a composition that contains two or more chemically/physically-linked compounds/drugs (e.g. by cross-linking, molecular agglomeration or binding to a common vehicle moiety), a composition that contains two or more compounds/drugs that are chemically or physically co-packaged (e.g. formulated in a liquid medium, particles (e.g. micron particles or nanoparticles) or materials on or inside the emulsion droplets, pharmaceutical kits, pharmaceutical packs, or patient packs, wherein two or more compounds/drugs are co-packaged or co-represented (e.g. a batch of dosage units).

The examples of a compound/drug composition with non-physical binding include: a material (e.g. non-single mixture) that contains at least one of the two or more compounds/drugs plus the instructions indicating at least one or more physical bindings that can be used to generate two or more compounds/drugs, a material (e.g. non-single mixture) that contains at least one of the two or more compounds/drugs plus instructions demonstrating a combination therapy utilizing two or more compounds/drugs, a material which contains at least one of the two or more compounds/drugs plus instructions for administration to a patient population, wherein the patient population has been treated with (or is taking) the other drug (others) of the two or more compounds/drugs, and a material that comprises at least one of the two or more compounds/drugs whose amount or form is specially formulated to be used in composition with the other (others) of the two or more compounds/drugs.

In this application, the term "combination therapy" is used herein to refer to therapy using the composition containing two or more compounds/drugs (as defined above). Thus, in the present invention, "combination therapy," "combination," as well as "composition" of compounds/drugs are used to refer to compounds/drugs administered as part of the complete treatment. Consequently, the posology of each of the two or more compounds/drugs may be different, suggesting that each can be administered at the same or at different times. It is important to understand that the compounds/drugs of said composition may be given in order (e.g. before or after) or concurrently (e.g., at the same time), and may be formulated either in the same pharmaceutical mixture (together) or in different mixtures (separately). Furthermore, simultaneous administration in the same mixture is given as a single mixture, and simultaneous administration in different mixtures is not given as a single mixture. In addition, the posology of each of the two or more compounds/drugs in a combination therapy may also vary in accordance with ways of administration.

These features and advantages of the present invention will be fully understood and appreciated from the following detailed description of the accompanying Drawings.

DETAILED DESCRIPTION OF THE PREFERRED EMBODIMENT

The present invention will now be described more specifically with reference to the following embodiments, which are provided for the purpose of demonstration rather than limitation.

EXAMPLE 1

Combination Therapy of Sorafenib and GW5074—cell Testing

Human renal carcinoma (ACHN) cells were cultured in Eagle MEM (Minimum Essential Medium) with 10% FBS (Fetal Bovine Serum) and 1% penicillin/streptomycin. Sulforhodamine B (SRB) is a negative protein with a sulfonic acid group and binds to basic amino acids of intracellular proteins in weak acidic conditions. The SRB protein was extracted from cells using weak alkaline solution and then subjected to absorbance measurement. The amount of intracellular proteins, which is an indicator for cell survival, can be calculated from the amount of SRB. ACHN or A498 cells were treated singularly with 2.5 µM sorafenib, 5 µM sorafenib, 10 µM sorafenib, GW5074, L779450 or PLX4720 for 24, 48 and 72 hours, followed by SRB assay to assess cell survival. Alternatively, ACHN cells were pre-treated with 10 µM GW5074, 10 µM L779450 or 10 µM PLX4720 for 30 minutes prior to 5 µM sorafenib treatment for additional 24, 48 and 72 hours, followed by SRB assay to assess growth inhibition.

Figure 1A:
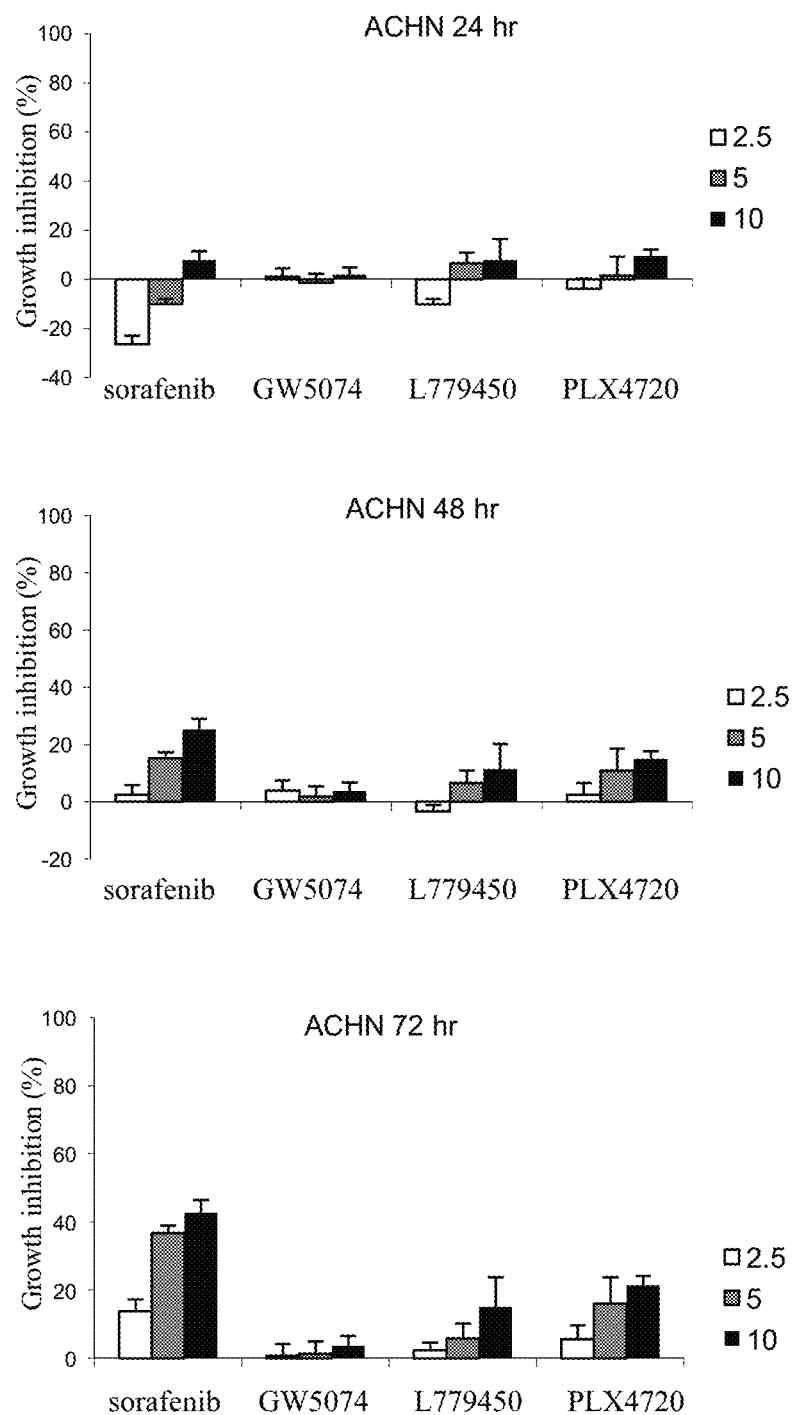
FIG. 1a shows growth inhibition of ACHN cells at 24, 48 and 72 hours after single-dose treatment of c-Raf inhibitors (sorafenib, GW5074, L779450 and PLX4720).
Figure 1B:
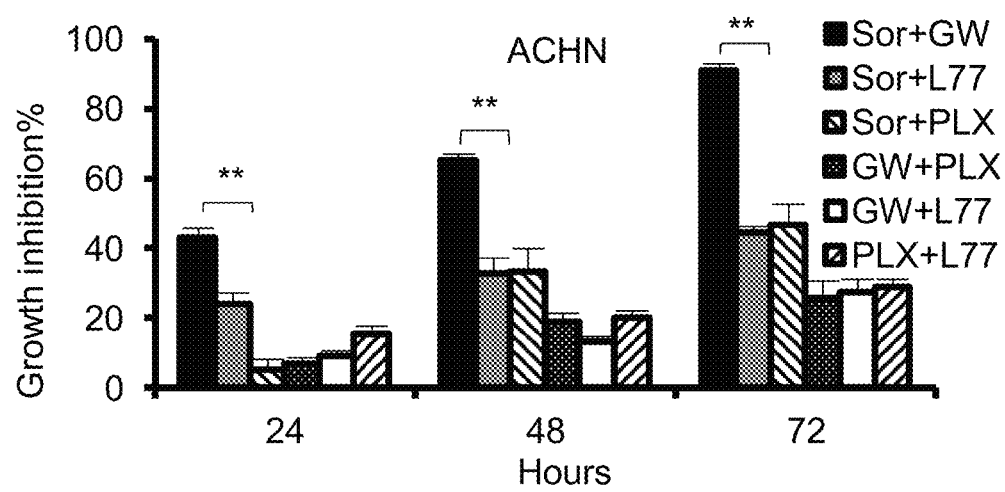
FIG. 1b shows growth inhibition of ACHN cells at 24, 48 and 72 hours after combination therapy of various c-Raf inhibitors (Sor: sorafenib, GW: GW5074, L77: L779450, PLX: PLX4720).

Based on the results, combination of c-Raf inhibitors comprising sorafenib and GW5074 showed no growth inhibition of cells following single low-dose treatment for 24 hours (5 µM sorafenib and 10 µM GW5074) (FIG. 1a, mean±S.D., n=4). However, combination of these two drugs not only induced cytotoxicity which was not observed in separate treatment of either drug originally, but successfully reduced side effects caused by effective dosage of sorafenib and inhibited cancer cell growth, suggesting a synergistic effect (FIG. 1b, mean±S.D., **$P<0.01$, n=4).

EXAMPLE 2

Combination Therapy of Sorafenib and GW5074—Xenograft

Six-week old immnunodeficient male mice (BALB/cAnN.Cg-Foxn1$^{nu}$/CrlNarl) with an average weight of 20 grams were xenografted with 1×10$^7$ ACHN cells to the right by intraperitoneal injection (i.p.). The mice were maintained in a specific pathogen-free (SPF) environment. The size of tumor was measured using a digital caliper twice a week and tumor volume was calculated by the equation of length*width*height*0.5. Drug administration which included 5 mg/kg sorafenib by oral gavage and subcutaneous injection of 10 mg/kg GW5074 once a day for three weeks was initiated when the tumor volume was >100 mm$^3$, and the size of tumor was measured every three days. A total of four groups were included in the experiment: a control group which received only vehicle (DMSO), and test groups administered with 5 mg/kg sorafenib, 25 mg/kg GW5074, or combination therapy of 5 mg/kg sorafenib and 25 mg/kg GW5074, respectively, with 8 mice in each group.

Figure 2:
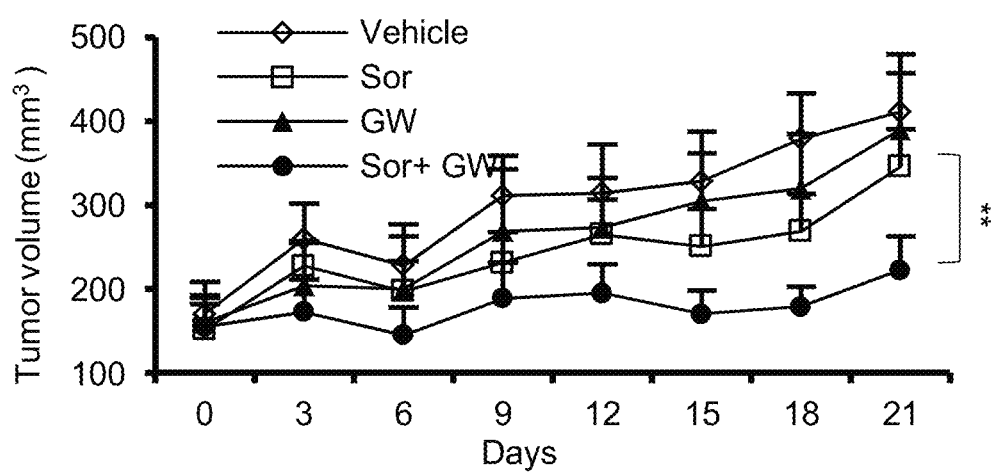
FIG. 2 shows the xenografted tumor volumes measured every 3 days for up to 21 days following sorafenib and GW5074 treatments administered singularly or in combination.

The results are shown in FIG. 2. Separate treatment of either 5 μM sorafenib or 10 μM GW5074 exhibited nearly no inhibition effect. In contrast, combination therapy of 5 μM sorafenib and 10 μM GW5074 demonstrated significant growth inhibition of ACHN cells (t-test, mean±SD, **P<0.01, n=8).

EXAMPLE 3

Combination Therapy of Sorafenib and GW5074—the Orthotopic Model

To simulate clinical phenomenon, we established an orthotopic spontaneous animal model for studying metastasis of renal carcinoma. First, ACHN cells were transfected with luciferase gene and the resulted Luc-ACHN transfectants (stable transfectants which express luciferase) with different expression status were then selected for in vivo culture in mice by subcutaneous injection. Six-week old and shaved mice were subcutaneously injected with $1 \times 10^7$ Luc-ACHN cells in 0.1 ml PBS. Two months after injection, the mice were sacrificed and their kidneys, livers, regional lymph nodes as well as other organs were collected for assessing tumor cells that were potentially metastatic, which was confirmed by hematoxylin-eosin (H&E) staining. Tumor cell lines that are highly metastatic were dissected in 1 ml PBS into small pieces aseptically and then cultured in MEM media containing 10% FBS (fetal bovine serum) and 1% penicillin/streptomycin following centrifugation. A few days later, monoclonal cell lines were first treated with trypsin to dissociate the cells and then cultured in vitro. The cells obtained from liver tumor tissues were named ACHN-L. The metastatic potential of various monoclonal cell lines collected from different organs was further analyzed by xenografting these tumor cells to the left kidneys of mice. The xenografted mice were sacrificed and examined 8 weeks after injection of tumor cells. Tumor growth observed in each organ was investigated through visual examination and histology procedures. The metastatic cells found in the liver were dissected into small pieces aseptically and cultured in vitro. The cells obtained from liver tumor tissues were named ACHN-L (subcutaneous injection) cells and the cells collected from the metastatic lesions after injection of ACHN-L cells to the left kidneys were called ACHN-LL cells. The same procedure using orthotopic xenograft of ACHN-LL cells and liver metastatic cells was repeated twice to select for highly metastatic tumors. The cancer cell line (Luc-ACHN-LL), which is highly metastatic and causes high mortality, was selected. Immunodeficient male mice was injected with $3 \times 10^5$ Luc-ACHN-LL cells in 50 μL PBS at the right renal capsule. In vivo luciferase activity was examined every day for up to three weeks so as to assure no leakage of cancer cells at the kidneys immediately after injection and to monitor metastasis of these cancer cells. Two to five minutes before utilizing the IVIS Xenogene system, 75 mg/kg D-Luciferin (Xenogen) in PBS was injected to the retro-orbital sinus of each mouse. Two weeks after injection of Luc-ACHN-LL cells, IVIS Xenogene system was used to monitor transfer of biological fluorescent images and to calculate the intensities of the photon signals (photons/s/cm$^2$/steradian). A total of five groups were included in the study: a control group which received only vehicle, and four test groups which respectively received 10 mg/kg sorafenib, 25 mg/kg GW5074, a combination therapy of 10 mg/kg sorafenib and 25 mg/kg GW5074 (the animals were fed with Sor 30 min post i.p. injection of GW), or 60 mg/kg sorafenib.

Figure 3:
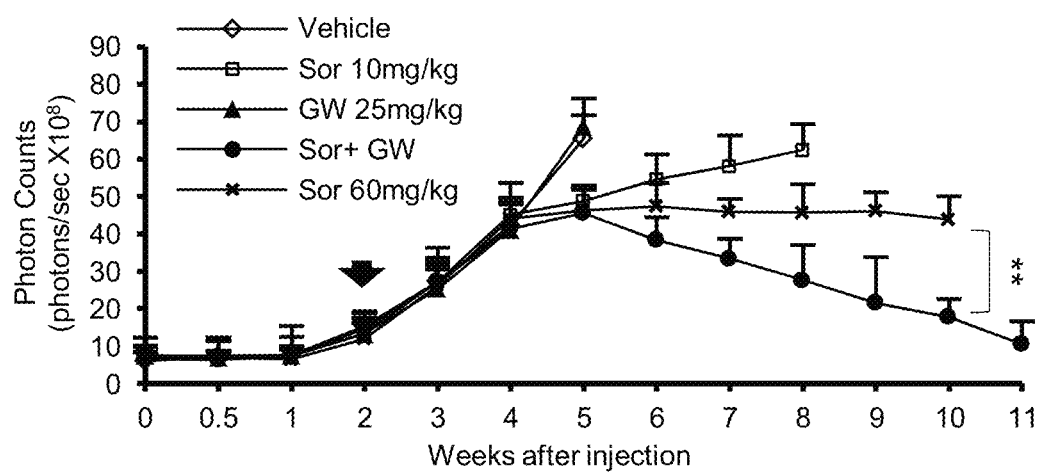
FIG. 3 shows the photon signals collected from the immnunodeficient mice orthotopic xenografted with Luc-ACHN-LL cells following treatments of various drugs. To calculate the number of tumors distributed throughout the body, the total photons emitted from the entire body of each mouse was measured as well as quantified by Xenogen® living image software. The arrow indicates the time of initial drug administration.

As shown in the results, the mice of the control group, 10 mg/kg sorafenib group, and 25 mg/kg GW5074 group died within 5, 8, and 5 weeks following injection of cancer cells, respectively. Likewise, loss of weight was also observed in the high-dose test group which received 60 mg/kg sorafenib, followed by death within 10 weeks. Surprisingly, only mice in the group which received low-dose combination therapy of 10 mg/kg sorafenib and 25 mg/kg GW5074 showed inhibition of both tumor sizes and metastasis of tumors as well as prolonged survival period in comparison with other groups. FIG. 3c shows the IVIS images and quantification of photon intensity, mean±SD, **P<0.01, n=4. In addition, the body weights as well as the energy of the mice that received combination therapy were similar to those observed in normal mice. The tumor cells collected from the mice which received combination therapy also showed profound cell necroptosis in comparison with other groups.

In summary, combination therapy of low-dose sorafenib and GW5074 is effective in growth inhibition of cancer cells in vitro. Also, most importantly, the efficacy of combination therapy can be examined in vivo in the condition which simulates clinical metastasis of cancer cells.

EXAMPLE 4

Combination therapy of sorafenib and GW5074 induces cell necroptosis through dephosphorylation of the death-associated DAPK at serine 308 followed by dissociation from proto-oncogene c-Raf. Cells were cultured as described in example 1, washed with phosphate buffered saline (PBS), and stained with annexin V-FITC and propidium iodide (PI) for 15 minutes. The presence of fluorescent Annexin V as well as propidium iodide (PI) was detected by flow cytometry so as to determine whether the cell death is caused by apoptosis or necrosis. The expression of c-Raf and DAPK as well as the phosphorylation status of DAPK were examined by Western blot and immunoprecipitation using antibodies. Anti-DAPK antibodies or non-immune rabbit IgG (IP: immunoglobulin) were included as negative controls, and cell survival was measured by SRB assay, as shown in example 1. In this experiment, ACHN cells were treated separately with DMSO (as a control group), 5 μM sorafenib, 10 μM GW5074, or combination therapy of 5 μM sorafenib and 10 μM GW5074 for 24 hours.

Figure 4A:
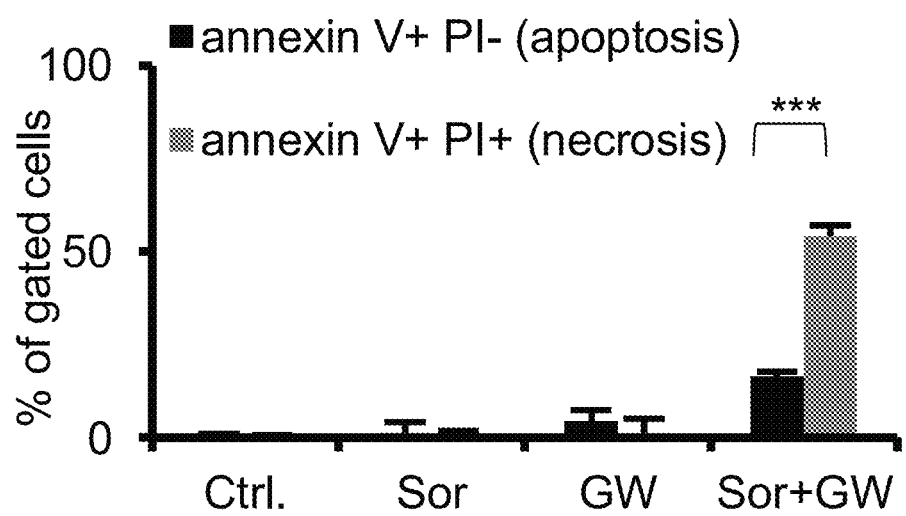
FIG. 4a shows the status of apoptosis or necrosis of ACHN cells at 24 hours following treatments of DMSO (control group), 5 µM sorafenib and 10 µM GW5074 or combination therapy.
Figure 4B:
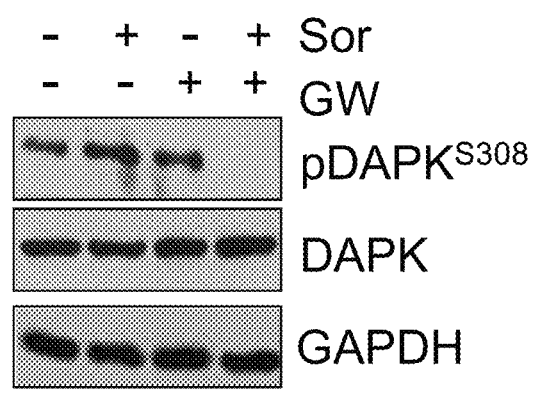
FIG. 4b shows the phosphorylation status of $pDAPK^{S308}$ and DAPK protein expression of ACHN cells at 24 hours following treatments of DMSO (control group), 5 µM sorafenib and 10 µM GW5074 or combination therapy by immunoblotting.
Figure 4C:
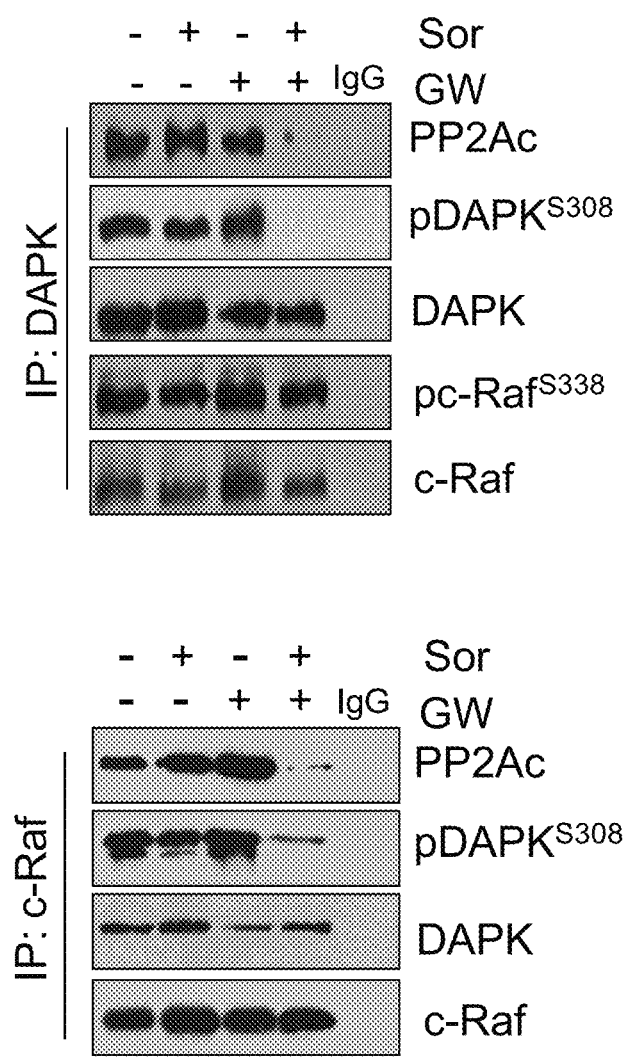
FIG. 4c shows the immunoprecipitation results of endogenous DAPK (upper) and c-Raf (lower) of ACHN cells at 24 hours after treatments of DMSO (control group), 5 µM sorafenib and 10 µM GW5074 or combination therapy, followed by immunoblotting to stain other relevant proteins using specific antibodies.
Figure 4D:
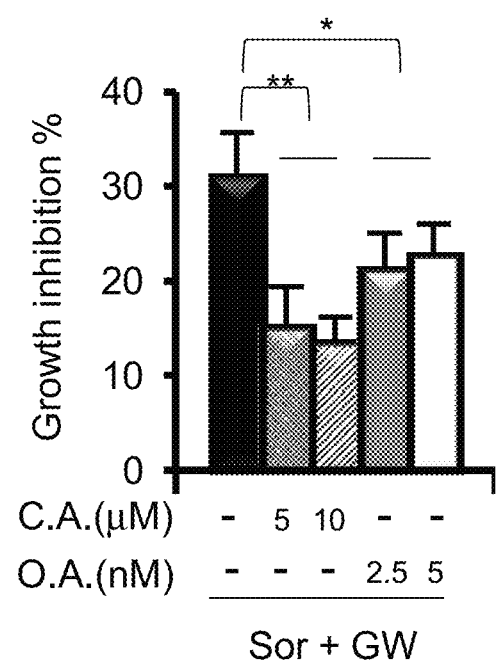
FIG. 4d shows growth inhibition of ACHN cells following combination therapy in the presence or absence of PP2A inhibitor: cantharidin (C.A.) or okadaic acid (O.A.).

The results indicated that the average cell necroptosis rate of ACHN cells treated with DMSO, monotherapy of 5 μM sorafenib, and monotherapy of 10 μM GW5074 was 0.37, 0.77, and 1.35%, respectively. However, cells which received combination therapy showed significant increase of necroptosis, up to 53.95% (FIG. 4a, t-test, mean±SD, ***P<0.001, n=4). Significant decrease in phosphate groups of S308 due to dephosphorylation of pDAPK$^{S308}$ by PP2A in tumor cells was only observed in cells treated with combination therapy (FIG. 4b). Results from immunoprecipitation further suggested c-Raf and DAPK, as well as PP2A, formed a complex. Combination therapy reduced the interactions among PP2A, DAPK and c-Raf, which subsequently decreased pDAPK$^{S308}$ (FIG. 4c). For the test group which received combination therapy, various concentrations of PP2A inhibitors (Cantharidin acid, C.A. and Okadaic acid, O.A.) were effective in inhibition of dephosphorylation of pDAPK$^{S308}$ and growth of ACHN cells only when provided 30 minutes prior to administration of the combination drugs (FIG. 4d, *P<0.05, **P<0.01, n=4).

Figure 4E:
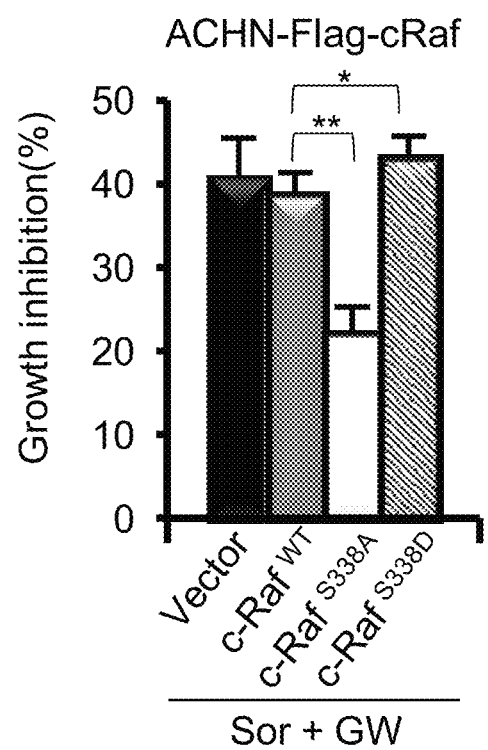
FIG. 4e shows growth inhibition of ACHN cells stably expressing wild-type or c-Raf mutants at 24 hours following combination therapy. (*$p<0.05$, **$p<0.01$ in comparison with wild type c-Raf).
Figure 4F:
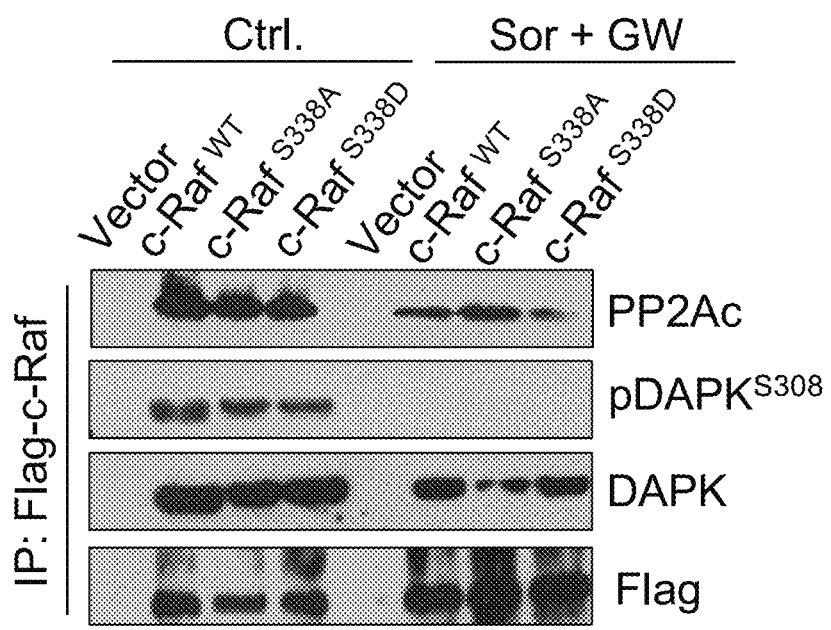
FIG. 4f is a protein expression profile of ACHN cells expressing flag-tagged-c-Raf or indicated mutants at 24 hours following DMSO (Ctrl.) treatment or combination therapy. Flag-c-Raf was immunoprecipitated from the cell lysates, followed by immunoblotting for indicated antibodies.

Next, the effects of combination therapy on the efficacy of pc-Raf$^{S338}$. Reduction of pDAPK$^{S308}$ noted as being most significant when ACHN cells were transfected with c-Raf$^{S338D}$ (simulation of phosphorylating S338). Moreover, c-Raf$^{S338A}$ (simulation of dephosphorylating S338) not only weakened dephosphorylation of DAPK S308, but also reduced growth inhibition of ACHN cells under combination therapy (FIG. 4e, *P<0.05, **P<0.01, n=3). In addition, immunoprecipitation results suggested that c-Raf$^{S338D}$ (simulation of phosphorylating S338) apparently lost its interaction with PP2A in comparison with c-Raf$^{WT}$ (wilt type) and c-Raf$^{S338A}$ (simulation of dephosphorylating S338) (FIG. 4f). Therefore, combination therapy not only increases pc-Raf$^{S338}$, but facilitates dephosphorylation of pDAPK$^{S308}$ by PP2A and enhances cell necroptosis.

The above-mentioned example reveals that combination therapy of sorafenib and GW5074 induces cell necroptosis through dephosphorylating serine 308 of death-associated protein kinase (DAPK) followed by dissociation from proto-oncogene c-Raf. Disassembly of c-Raf and DAPK can also be used as the target for future drug design, which is dissociation of c-Raf from DAPK in cells leads to initiation of cell necroptosis process which kills cells effectively.

EXAMPLE 5

Methods of Drug Screening Using In Vitro Biomarkers

Previous studies showed that dephosphorylation of DAPK at serine 308 can be used as a predictive biomarker for anticancer effects of drugs on cancer cells. The methods for cell culture as well as detection for examining growth inhibition are as described in example 1. ACHN, 786-O and Rcc-Sut-002 (drug-resistant cancer cells) cell lines were treated with siRNA of type a and type b DAPK (siDAPK-a, sense strand: 5'-CAAGAAACGUUAGCAAAUGUU-3' [SEQ ID No:3] and antisense strand: 5'-CAUUUGC-UAACGUUUCUUGUU-3' [SEQ ID No:4]; siDAPK-b, sense strand: 5'-GGUCAAGGAUCCAAAGAAGUU-3' [SEQ ID No:5] and antisense strand 5'-CUUCUUUG-GAUCCUUGACCUU-3' [SEQ ID No:6]). Each cell line was analyzed by siDAPK-a, siDAPK-b and a control (Scr). Growth inhibition of cells was examined following combination therapy of 5 μM sorafenib and 10 μM GW5074 for 24 hr. On the other hand, HeLa cells and MDA-MB-231 cells were transfected with the control empty vector (vector), WT (wild type), $DAPK^{S308D}$, $DAPK^{S308A}$ or $DAPK^{K42A}$ (inactivated protein kinase), and growth inhibition of the transfected cells was examined following combination therapy of 5 μM sorafenib and 10 μM GW5074 for 24 hours.

Figure 5A:
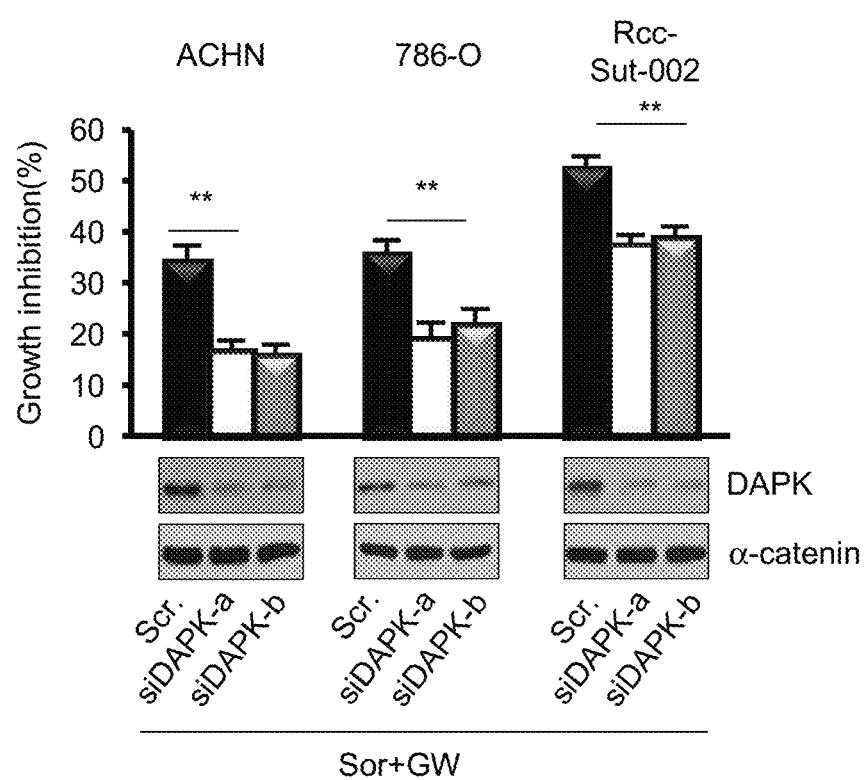
FIG. 5a shows growth inhibition of ACHN, 786-O and Rcc-Sut-002 cells transfected with scrambled siRNA (Scr), DAPK siRNA1 (siDAPK-a), or DAPK siRNA2 (siDAPK-b) following combination therapy (upper panel). DAPK and □-catenin expression of the cell lysates were examined by immunoblotting (lower panel).
Figure 5B:
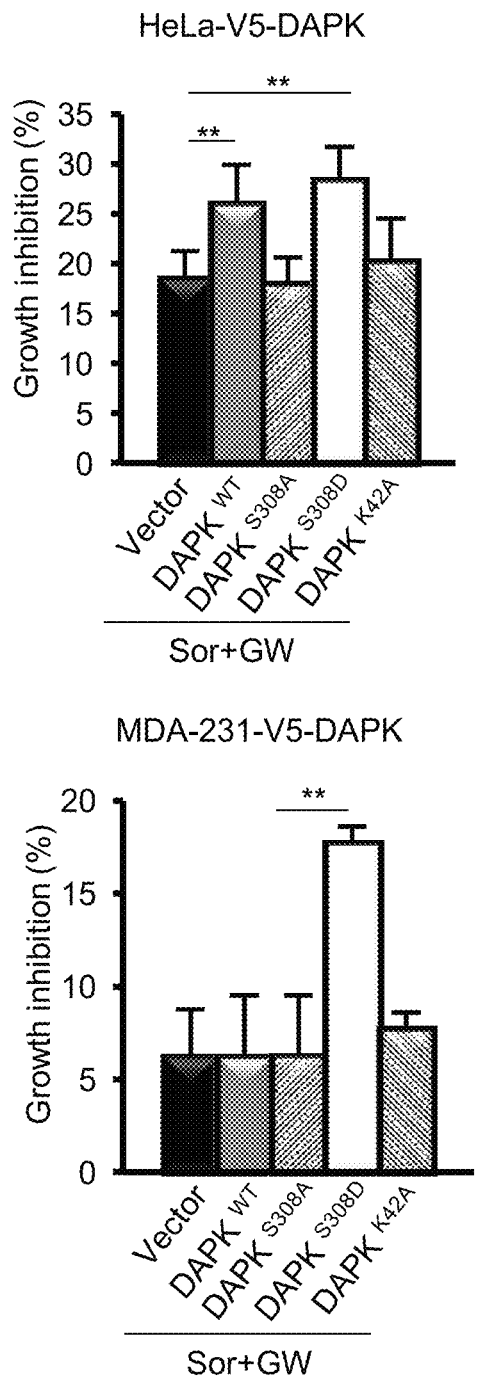
FIG. 5b shows growth inhibition of HeLa (left panel), MDA-MB231 cells expressing V5-tagged-DAP (right panel) and indicated mutants at 24 hours following combination therapy.

The results indicated that DAPK protein is indispensible for cytotoxicity induced by combination therapy of sorafenib and GW5074. In ACHN, 786-O and RCC-SUT-002 cells, growth inhibition resulting from two siRNAs capable of inhibiting DAPK expression was reduced by around 60% (FIG. 5a). Furthermore, phosphorylation of DAPK at S308 is highly associated with cytotoxicity induced by combination therapy. Overexpression of $DAPK^{WT}$ and $DAPK^{S308D}$ in HeLa cells which usually express higher $pDAPK^{S308}$ notably increased the cytotoxicity after receiving combination therapy, whereas cell death was not enhanced in $DAPK^{K42A}$ (inactivated DAP kinase) and $DAPK^{S308A}$ (simulation of non-phosphorylation of S308) following combination therapy. Only $DAPK^{S308D}$ was found to increase growth inhibition in MDA-MB-231 breast cancer cells which usually express lower $pDAPK^{S308}$ after receiving combination therapy. The rest, including $DAPK^{WT}$, $DAPK^{S308A}$, and $DAPK^{K42A}$, showed no increase in growth inhibition (FIG. 5b, mean±SD, **p<0.01, n=3). According to the results, it is not the DAPK protein itself, but S308 phosphorylation of DAPK which plays a key role in inducing cytotoxicity when treated with combination therapy of sorafenib and GW5074. This is because dephosphorylation of S308 is not effective under combination therapy even with higher DAPK expression. The cytotoxicity effect induced by combination therapy must go through activated DAP K. Therefore combination therapy of sorafenib and GW5074 is only effective in the presence of $pDAPK^{S308}$ in cancer cells.

Phosphorylation of c-Raf protein can be used as a biomarker for predicting the anticancer effect of drugs on cancer cells. Reduction of $pDAPK^{S308}$ is most evident in ACHN cells transfected with c-$Raf^{S338D}$ (simulating phosphorylation of S388). Not only does c-$Raf^{S338A}$ (simulating dephosphorylation of S388) reduce dephosphorylation of DAPK S308, but also decreases growth inhibition of ACHN cells under combination therapy (FIG. 4e, *P<0.05, **P<0.01, n=3). Thus, S338 phosphorylation of c-Raf is beneficial for combination therapy due to better treatment effects, and c-Raf S338D (simulating phosphorylation of S388) has a better effect in comparison with c-Raf S338A (simulating dephosphorylation of S388).

Figure 5C:
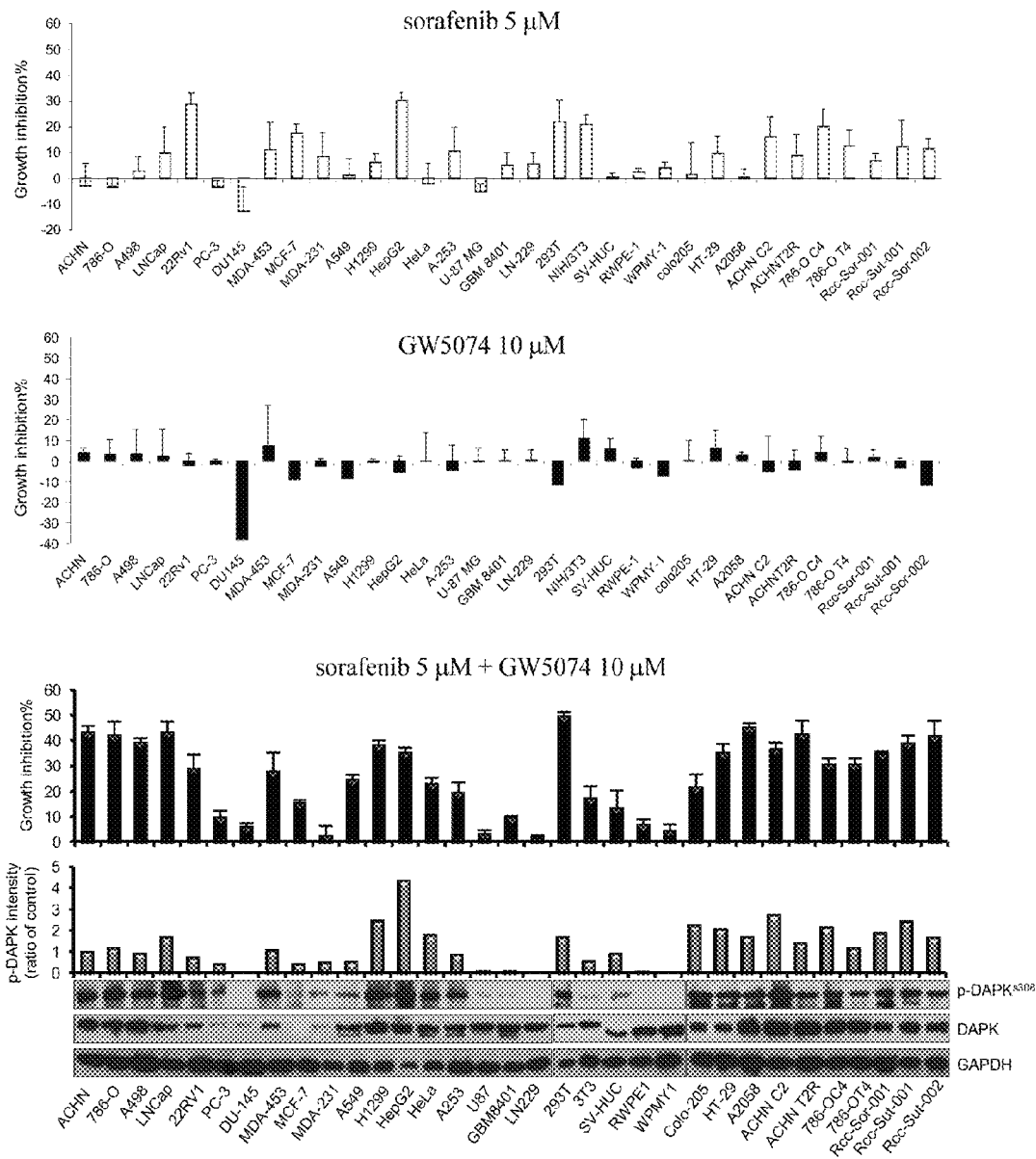
FIG. 5c shows growth inhibition of various cancer cells or normal cells at 24 hours following treatments of 5 µM sorafenib, 10 µM GW5074, or combination therapy. The lowest part indicates the phosphorylation status of $pDAPK^{S308}$ of ACHN group in comparison with the control group. The expression of $pDAPK^{S308}$ and DAPK was detected by immunoblotting.
Figure 5D:
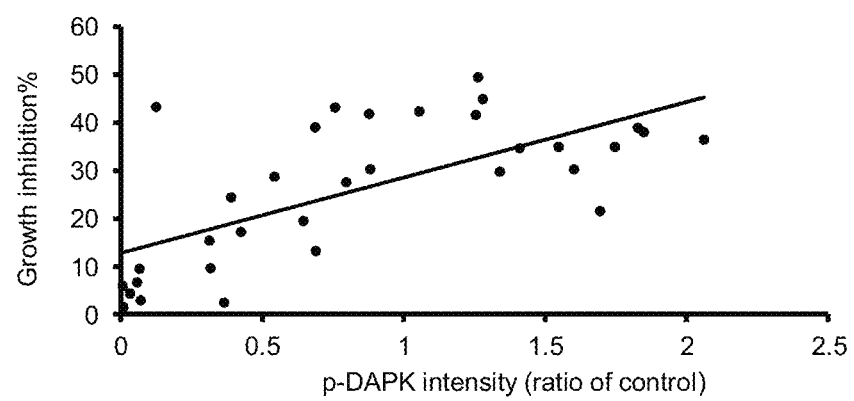
FIG. 5d is a regression plot demonstrating the correlation between the expression of $pDAPK^{S308}$ and growth inhibition of cells. $R^2=0.4551$, $R=0.6746$, $p=0.00001$.

In addition, a number of cancer cells as well as normal cells were examined. It was found that combination therapy caused only limited cytotoxicity in the above-mentioned cells due to low S308 phosphorylation of DAPK in normal fibroblasts and epithelial cells. Nonetheless, growth inhibition caused by combination therapy among various tumor cells is positively correlated with the status of S308 phosphorylation of DAPK (FIGS. 5c and 5d, mean±SD, **p<0.01, n=3). It was further investigated as to whether combination therapy has an inhibition effect on drug-resistant cancer cells using sorafenib-resistant cancer cells obtained from clinical cases (RCC-Sut-001, RCC-Sut-002, RCC-Sor-001) and animal models (786-OT4, ACHN-T2R). All drug-resistant cancer cells that have highly phosphorylated DAPK S308 were significantly inhibited under combination therapy. Moreover, HT29 and A2058 cancer cell lines that are both Raf inhibitors-resistant showed high S308 phosphorylation of DAPK as well, and combination therapy demonstrated significant inhibition as well as synergistic effect (FIG. 5c and Table 1). Additionally, because S308 phosphorylation of DAPK in normal cells are relatively low, growth inhibition of cancer cells induced by combination therapy of sorafenib and GW5074 are therefore selective and cause no toxicity in normal cells.

TABLE 1

| | | | |
|---|---|---|---|
| 1 | ACHN | renal cell adenocarcinoma | |
| 2 | 786-O | renal cell adenocarcinoma | |
| 3 | A498 | renal cell adenocarcinoma | |
| 4 | LNCap | prostate carcinoma | |
| 5 | 22RV1 | prostate carcinoma | |
| 6 | PC-3 | prostate carcinoma | |
| 7 | DU-145 | prostate carcinoma | |
| 8 | MDA-453 | breast adenocarcinoma | |
| 9 | MCF-7 | breast adenocarcinoma | |
| 10 | MDA-231 | breast adenocarcinoma | |
| 11 | A549 | lung carcinoma | |
| 12 | H1299 | non-small cell lung cancer | |
| 13 | HepG2 | hepatocellular carcinoma | |
| 14 | HeLa | cervix carcinoma | |
| 15 | A253 | submaxillary salivary gland carcinoma | |
| 16 | U87 | glioblastoma; astrocytoma | |
| 17 | GBM8401 | brain malignant glioma | |
| 18 | LN229 | glioblastoma | |
| 19 | 293T | kidney epithelial | |
| 20 | 3T3 | embryo fibroblast | |
| 21 | SV-HOC | uroepithelium epithelial | |
| 22 | RWPE1 | prostate normal epithelial cell | |
| 23 | WPMY1 | prostate normal epithelial cell | |
| 24 | Colo-205 | colorectal adenocarcinoma | |
| 25 | HT-29 | colorectal adenocarcinoma | |
| 26 | A2058 | melanoma | B-Raf mutation |
| 27 | ACHNC2 | drug-resistant renal cell adenocarcinoma cell | Acquired resistant |
| 28 | ACHNT2R | drug-resistant renal cell adenocarcinoma cell | Acquired resistant |
| 29 | 786-OC4 | drug-resistant renal cell adenocarcinoma cell | Acquired resistant |
| 30 | 786-OT4 | drug-resistant renal cell adenocarcinoma cell | Acquired resistant |
| 31 | RCC-Sor-001 | drug-resistant renal cell adenocarcinoma cell | Acquired resistant |
| 32 | RCC-Sut-001 | drug-resistant renal cell adenocarcinoma cell | Acquired resistant |
| 33 | RCC-Sut-002 | drug-resistant renal cell adenocarcinoma cell | Acquired resistant | c-Raf and DAPK are found in cytoplasm and mitochondria. Combination therapy leads to relocation of DAPK between cytoplasm and mitochondria, along with dephosphorylation of $pDAPK^{S308}$ by PP2A. Dephosphorylated DAPK decreases its interaction with c-Raf in cytoplasm. In addition, only DAPK$^{S308D}$ can be induced to be translocated from mitochondria to cytoplasm of MDA-MB-231 under combination therapy. This results in production of ROS and low phosphorylation of pDAPK$^{S308}$. However, reduction of both c-Raf and phosphorylation of its S338 induced by combination therapy in cytoplasm and mitochondria was found only in cancer cells with highly phosphorylated pDAPK$^{S308}$ and not in cancer cells with low pDAPK$^{S308}$.

EXAMPLE 6

Figure 6A:
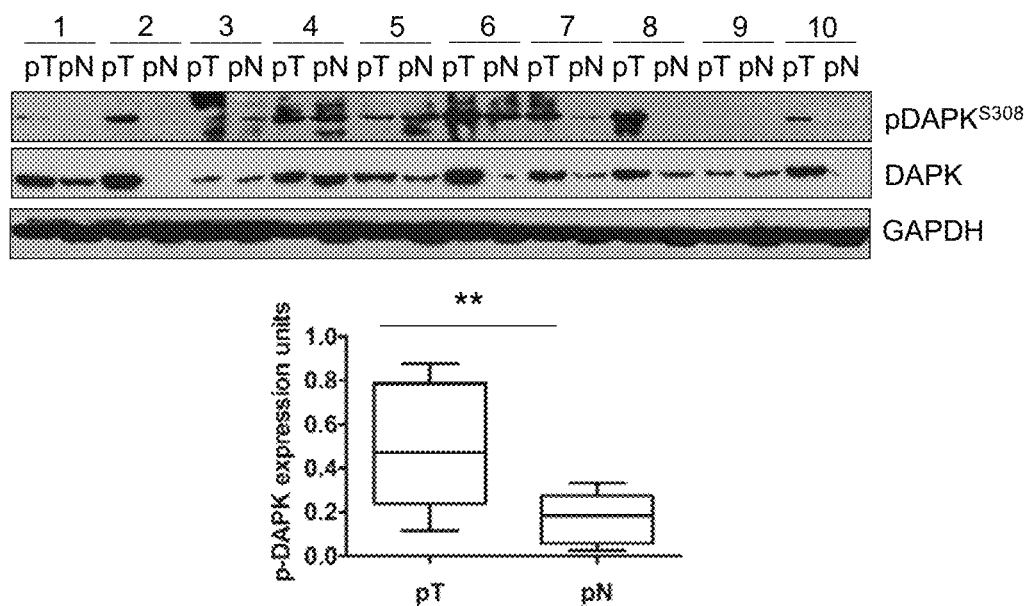
FIG. 6a shows the expression status of $pDAPK^{S308}$ and DAPK in tumors (pT) or normal tissues (pN) (upper) of the same patient by immunoblotting. The lower panel indicates the relative intensity of $pDAPK^{S308}$ after normalized to GAPDH expression.
Figure 6B:
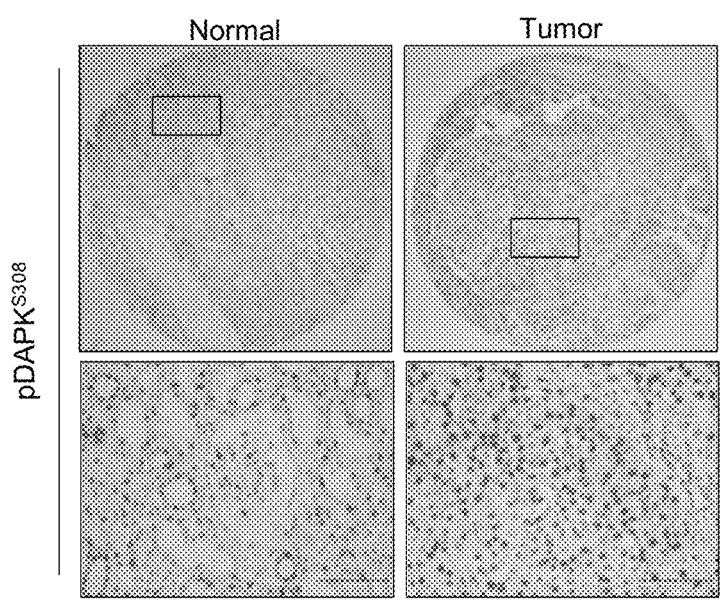
FIG. 6b is the immnunohistochemical (IHC) analysis of $pDAPK^{S308}$ expression of human normal and renal carcinoma tissues. Original magnification, ×40 (upper panel), ×100 (lower panel), scale bars is 100 □M
Figure 6C:
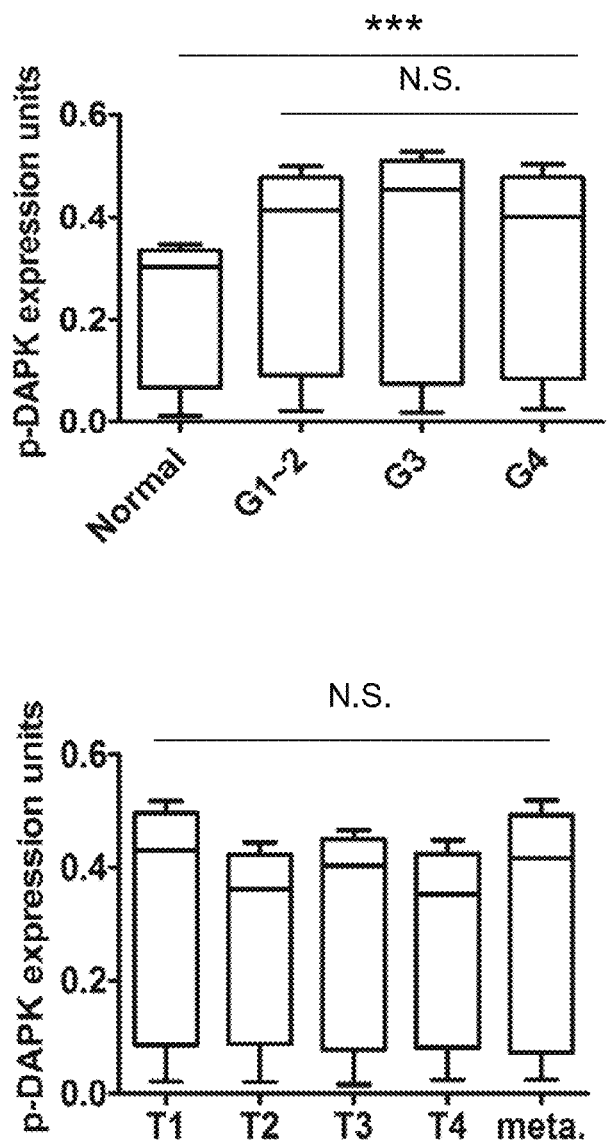
FIG. 6c shows $pDAPK^{S308}$ expression of human normal and renal cancer tissues after quantification using microarrays. The upper indicates normal as well as different grades (G), and the lower shows different stages (T) as well as metastasis of cancer cells (meta.).

The tumor samples and normal tissue samples collected from 20 patients with renal cell carcinoma were further investigated. Based on the Western blot results, 16 out of 20 samples showed elevated phosphorylation of DAPK at S308 in cancer cells in comparison with normal tissue samples (FIG. 6d. (pDAPK$^{S308}$/GAPDH, mean±S.D., **p<0.005). Immnunohistochemical (IHC) analysis also demonstrated that S308 phosphorylation of DAPK was higher in 181 human renal carcinoma samples in comparison with normal kidney tissues (FIG. 6b). On the other hand, S308 phosphorylation of DAPK showed no significant differences between different grades (G) or stages (T) of the cancer using tissue microarray (TMA) and semi-quantitative analysis. The results suggested that pDAPK$^{S308}$ is not only a factor for determining prognosis, but also a predictive biomarker of combination therapy for treating kidney cancers.

Figure 6D:
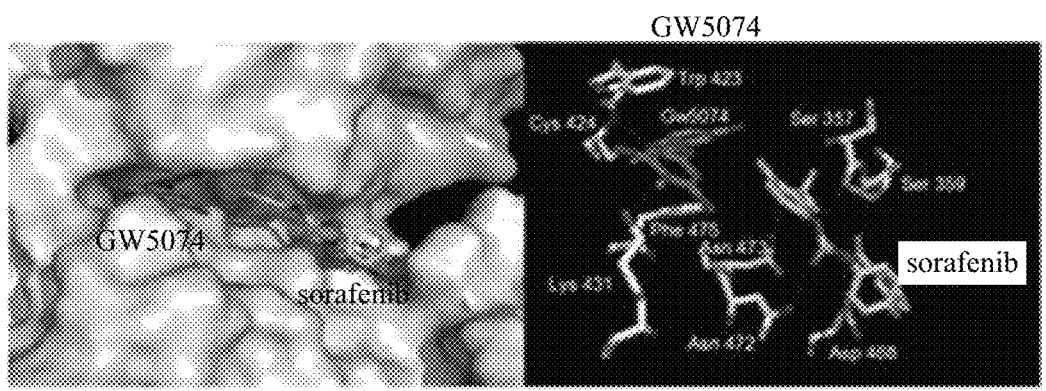
FIG. 6d is a computer simulation photo demonstrating the conformation of c-Raf kinase after interaction with sorafenib and GW5074. Green represents GW5074 and magenta represents sorafenib.

According to the results, a computer simulation experiment was then conducted to assess the crystal structures of various c-Raf inhibitors bound with c-Raf. The maximal energy was expected to be produced by binding of inhibitors to the structural region of c-Raf kinase when the combination of GW5074 and sorafenib binds to c-Raf (−182 kcal/mole, Table 2). GW5074 at the front end binds with c-Raf and produces a deeper hydrophobic pocket for binding through Ile355, Val363, Ala373, Leu406, Trp423 and Phe47. Under the circumstances, more regions in the hydrophobic pocket will be occupied by GW5074 and sorafenib (as shown in FIG. 6d).

TABLE 2

Various inhibitors bind to c-Raf separately or in combinations

| Inhibitor | | Binding energy (kcal/mole) |
|---|---|---|
| Name | Structure | |
| sorafenib | [structure] | −82 |
| + L779450 | | −134 |
| + GW5074 | | −125 |
| + PLX44720 | | −113 |
| GW5074 | [structure] | −128 |
| + Sorafenib | | −182 |
| PLX44720 | [structure] | −77 |
| + sorafenib | | −140 |
| L779450 | [structure] | −60 |
| + sorafenib | | −125 |

The present invention discloses a novel combination therapy for treating cancer by utilizing a composition that comprises sorafenib and GW5074. The combination therapy is not toxic to normal cells due to selective inhibition on cancer cells. Therefore, this therapy is safe and very promising for future applications. The efficacy of the combination therapy was verified by using pDAPKS308 as a predictive biomarker so as to avoid unnecessary treatments. The research of the present invention overcomes the obstacles faced by current studies for cancer therapies and meets the requirements of an ideal model for preclinical treatments.

Many changes and modifications in the above described embodiment of the invention can, of course, be carried out without departing from the scope thereof. Accordingly, to promote the progress in science and the useful arts, the invention is disclosed and is intended to be limited only by the scope of the appended claims.

What is claimed is:

1. A method for treating cancer in a subject in need thereof, comprising the steps of,
   (a) detecting whether the cancer cells of the subject expresses phosphorylation on serine 308 of death-associated protein kinase (DAPK); and
   (b) administering to the subject (1) an effective amount of sorafenib or a pharmaceutically acceptable salt thereof, and (2) an effective amount of 3-(3,5-Dibromo-4-hydroxy-benzylidene)-5-iodo-1,3-dihydro-indol-2-one or a pharmaceutically acceptable salt thereof, when the phosphorylation on serine 308 of DAPK in the cancer cells is detected.

2. The method of claim 1, wherein the sorafenib or a pharmaceutically acceptable salt thereof and the 3-(3,5-Dibromo-4-hydroxy-benzylidene)-5-iodo-1,3-dihydro-indol-2-one or a pharmaceutically acceptable salt thereof are administered concurrently.

3. The method of claim 1, wherein the sorafenib or a pharmaceutically acceptable salt thereof and the 3-(3,5-Dibromo-4-hydroxy-benzylidene)-5-iodo-1,3-dihydro-indol-2-one or a pharmaceutically acceptable salt thereof are administered separately.

4. The method of claim 1, wherein the sorafenib or a pharmaceutically acceptable salt thereof and the 3-(3,5-Dibromo-4-hydroxy-benzylidene)-5-iodo-1,3-dihydro-indol-2-one or a pharmaceutically acceptable salt thereof are formulated in a single composition that further comprises one or more pharmaceutically acceptable vehicles.

5. The method of claim 4, wherein the pharmaceutically acceptable vehicle is selected from the group consisting of, excipients, diluents, thickeners, fillers, binders, disintegrants, lubricants, oil or non-oil agents, surfactants, suspending agents, gelling agents, adjuvants, preservatives, antioxidants, stabilizers, and coloring agents.

6. The method of claim 4, wherein the composition is given by oral administration, immersion, injection, topical applications, or patch administration.

7. The method of claim 1, wherein the sorafenib or a pharmaceutically acceptable salt thereof and the 3-(3,5-Dibromo-4-hydroxy-benzylidene)-5-iodo-1,3-dihydro-indol-2-one or a pharmaceutically acceptable salt thereof are respectively formulated into two compositions, with each composition further comprises one or more pharmaceutically acceptable vehicles.

8. The method of claim 7, wherein the pharmaceutically acceptable vehicle is selected from the group consisting of, excipients, diluents, thickeners, fillers, binders, disintegrants, lubricants, oil or non-oil agents, surfactants, suspending agents, gelling agents, adjuvants, preservatives, antioxidants, stabilizers, and coloring agents.

9. The method of claim 7, wherein each composition is given by oral administration, immersion, injection, topical applications, or patch administration.

10. The method of claim 7, wherein the two compositions are administered separately.

11. A method for treating cancer in a subject in need thereof, in which the cancer cell of the subject expresses phosphorylation on serine 308 of death-associated protein kinase (DAPK), the method comprises the steps of: administering to the subject (1) an effective amount of sorafenib or a pharmaceutically acceptable salt thereof, and (2) an effective amount of 3-(3,5-Dibromo-4-hydroxy-benzylidene)-5-iodo-1,3-dihydro-indol-2-one or a pharmaceutically acceptable salt thereof.

12. The method of claim 11, wherein the sorafenib or a pharmaceutically acceptable salt thereof and the 3-(3,5-Dibromo-4-hydroxy-benzylidene)-5-iodo-1,3-dihydro-indol-2-one or a pharmaceutically acceptable salt thereof are administered concurrently.

13. The method of claim 11, wherein the sorafenib or a pharmaceutically acceptable salt thereof and the 3-(3,5-Dibromo-4-hydroxy-benzylidene)-5-iodo-1,3-dihydro-indol-2-one or a pharmaceutically acceptable salt thereof are administered separately.

14. The method of claim 11, wherein the sorafenib or a pharmaceutically acceptable salt thereof and the 3-(3,5-Dibromo-4-hydroxy-benzylidene)-5-iodo-1,3-dihydro-indol-2-one or a pharmaceutically acceptable salt thereof are formulated in a single composition that further comprises one or more pharmaceutically acceptable vehicles.

15. The method of claim 14, wherein the pharmaceutically acceptable vehicle is selected from the group consisting of, excipients, diluents, thickeners, fillers, binders, disintegrants, lubricants, oil or non-oil agents, surfactants, suspending agents, gelling agents, adjuvants, preservatives, antioxidants, stabilizers, and coloring agents.

16. The method of claim 14, wherein the composition is given by oral administration, immersion, injection, topical applications, or patch administration.

17. The method of claim 11, wherein the sorafenib or a pharmaceutically acceptable salt thereof and the 3-(3,5-Dibromo-4-hydroxy-benzylidene)-5-iodo-1,3-dihydro-indol-2-one or a pharmaceutically acceptable salt thereof are respectively formulated into two compositions, with each composition further comprises one or more pharmaceutically acceptable vehicles.

18. The method of claim 17, wherein the pharmaceutically acceptable vehicle is selected from the group consisting of, excipients, diluents, thickeners, fillers, binders, disintegrants, lubricants, oil or non-oil agents, surfactants, suspending agents, gelling agents, adjuvants, preservatives, antioxidants, stabilizers, and coloring agents.

19. The method of claim 17, wherein each of the two compositions is given by oral administration, immersion, injection, topical applications, or patch administration.

20. The method of claim 17, wherein the two compositions are administered separately.

* * * * *